United States Patent
Drewes, Jr. et al.

(10) Patent No.: US 9,365,018 B2
(45) Date of Patent: Jun. 14, 2016

(54) METHOD OF FORMING REINFORCED TUBING

(75) Inventors: David A. Drewes, Jr., Bloomington, IN (US); Brett O. Baker, Ellettsville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 1220 days.

(21) Appl. No.: 13/128,108

(22) PCT Filed: Nov. 16, 2009

(86) PCT No.: PCT/US2009/064519
§ 371 (c)(1),
(2), (4) Date: Jul. 21, 2011

(87) PCT Pub. No.: WO2010/059542
PCT Pub. Date: May 27, 2010

(65) Prior Publication Data
US 2011/0282288 A1 Nov. 17, 2011

Related U.S. Application Data

(60) Provisional application No. 61/117,385, filed on Nov. 24, 2008.

(51) Int. Cl.
*B23B 37/00* (2006.01)
*B32B 37/00* (2006.01)
(Continued)

(52) U.S. Cl.
CPC .............. *B32B 37/00* (2013.01); *A61M 25/005* (2013.01); *A61M 25/0012* (2013.01); *B05D 1/00* (2013.01);
(Continued)

(58) Field of Classification Search
CPC ........................................................ B05D 1/00
USPC ................. 604/280, 524; 156/218, 227, 247; 264/103; 427/2.1
See application file for complete search history.

(56) References Cited

U.S. PATENT DOCUMENTS 4,764,324 A * 8/1988 Burnham ................ 264/103
5,380,304 A    1/1995 Parker .................... 604/282
(Continued)

FOREIGN PATENT DOCUMENTS

EP    0430542 A2    6/1991
JP    3-500626 A    2/1991
(Continued)

OTHER PUBLICATIONS

Declaration by David A. Drewes, Jr. (co-inventor) dated Dec. 14, 2015.

*Primary Examiner* — Dah-Wei D Yuan
*Assistant Examiner* — Andrew Bowman
(74) *Attorney, Agent, or Firm* — Brinks Gilson & Lione

(57) ABSTRACT

A method of forming a reinforced tubular medical device in a continuous operation, and a medical device formed by the continuous method. An elongated core capable of movement about a line is provided. An elongated tubular member is formed around a moving length of the core by extruding a coating of a functionalized polymer around the moving core length, applying a reinforcing member to an outer surface of the functionalized polymer coating along the moving length, and extruding a polymeric outer jacket over the functionalized polymer and reinforcing member along the moving length, such that a bond is formed between the functionalized polymer and the polymeric outer jacket. The elongated tubular member is cut to desired length to form the tubular medical device, and the core is removed from the device.

18 Claims, 2 Drawing Sheets

(51) Int. Cl.

| | | |
|---|---|---|
| *B05D 1/00* | (2006.01) | |
| *A61M 25/00* | (2006.01) | |
| *B29D 23/00* | (2006.01) | |
| *B32B 1/08* | (2006.01) | |
| *F16L 11/08* | (2006.01) | |
| *B32B 7/12* | (2006.01) | |
| *B32B 27/08* | (2006.01) | |
| *B32B 27/28* | (2006.01) | |
| *B32B 27/32* | (2006.01) | |
| *B32B 27/34* | (2006.01) | |
| *B32B 27/40* | (2006.01) | |
| *B29C 47/00* | (2006.01) | |
| *B29C 53/12* | (2006.01) | |
| *B29C 65/00* | (2006.01) | |
| *B29K 71/00* | (2006.01) | |
| *B29K 77/00* | (2006.01) | |
| *B29L 9/00* | (2006.01) | |
| *B29L 31/00* | (2006.01) | |

(52) U.S. Cl.
CPC .......... *B29C 47/0026* (2013.01); *B29D 23/001* (2013.01); *B32B 1/08* (2013.01); *B32B 7/12* (2013.01); *B32B 27/08* (2013.01); *B32B 27/285* (2013.01); *B32B 27/32* (2013.01); *B32B 27/322* (2013.01); *B32B 27/34* (2013.01); *B32B 27/40* (2013.01); *F16L 11/081* (2013.01); *B29C 47/00* (2013.01); *B29C 53/12* (2013.01); *B29C 66/8122* (2013.01); *B29K 2071/00* (2013.01); *B29K 2077/00* (2013.01); *B29L 2009/005* (2013.01); *B29L 2031/7542* (2013.01); *B32B 2250/24* (2013.01); *B32B 2307/412* (2013.01); *B32B 2307/714* (2013.01); *B32B 2307/736* (2013.01); *B32B 2535/00* (2013.01)

(56) References Cited

U.S. PATENT DOCUMENTS

| | | | | |
|---|---|---|---|---|
| 5,904,670 | A | * | 5/1999 | Schreiner ............... 604/523 |
| 6,911,509 | B1 | | 6/2005 | Chung et al. ............. 526/197 |
| 7,115,685 | B2 | | 10/2006 | Wynne et al. ............. 525/326.2 |
| 7,220,807 | B2 | | 5/2007 | Chung et al. ............. 526/197 |
| 2001/0034514 | A1 | | 10/2001 | Parker ..................... 604/525 |
| 2002/0132076 | A1 | | 9/2002 | Stevens ................... 428/35.8 |
| 2003/0135198 | A1 | * | 7/2003 | Berhow et al. ........... 604/524 |
| 2005/0074570 | A1 | | 4/2005 | Agrawal .................. 428/36.91 |
| 2007/0074805 | A1 | | 4/2007 | Leeflang et al. .......... 156/84 |
| 2007/0169877 | A1 | * | 7/2007 | Leeflang et al. .......... 156/218 |

FOREIGN PATENT DOCUMENTS

| | | | | |
|---|---|---|---|---|
| JP | 04341836 | | 11/1992 | |
| JP | 06-142207 | A | 5/1994 | |
| JP | 2007-000392 | A | 1/2007 | |
| JP | 2007000392 | * | 1/2007 | ............... A61L 33/00 |
| WO | WO 90/01406 | | 2/1990 | |
| WO | WO 96/38193 | A1 | 12/1996 | |
| WO | WO 2006/085498 | A | 8/2006 | |

\* cited by examiner

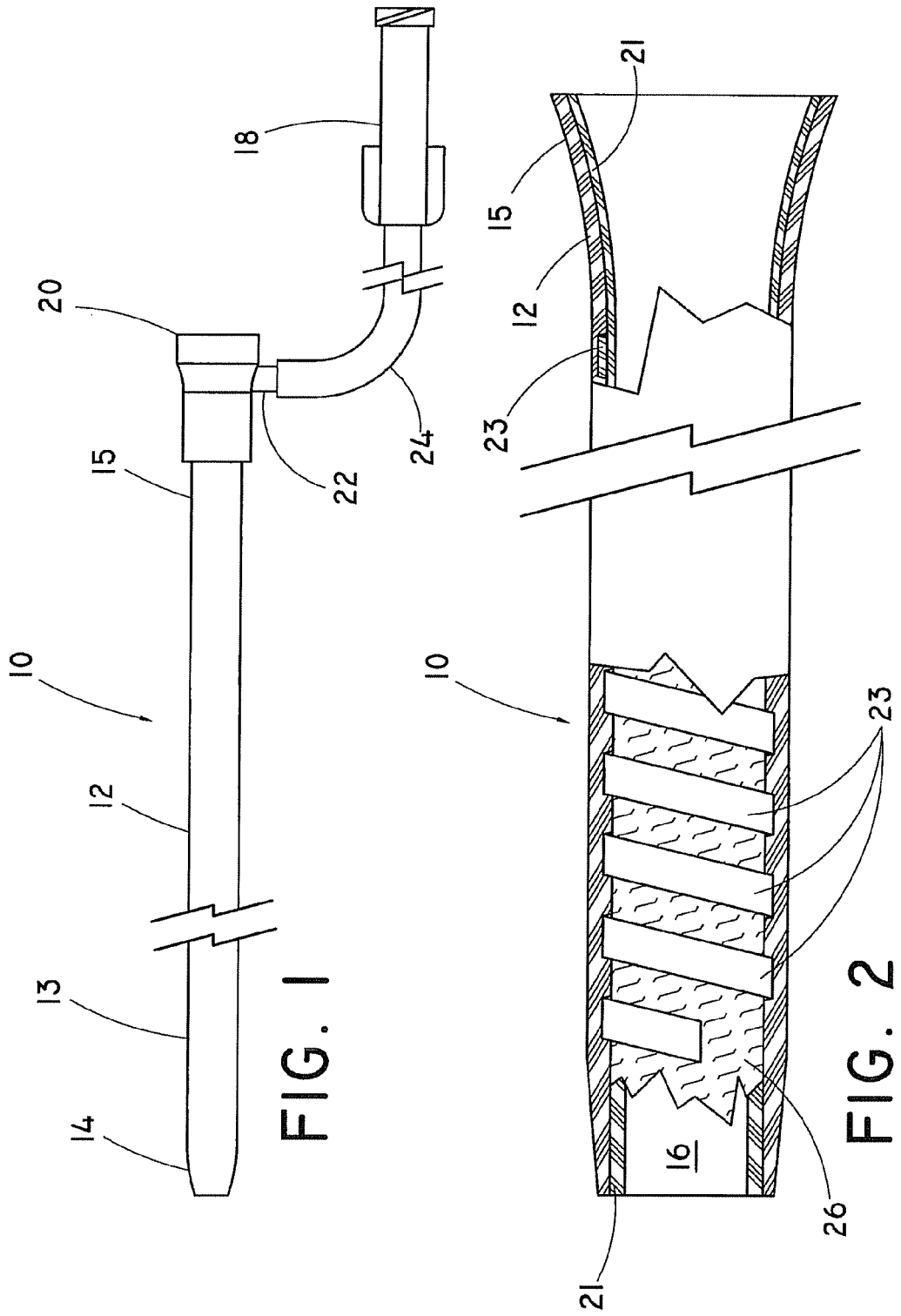

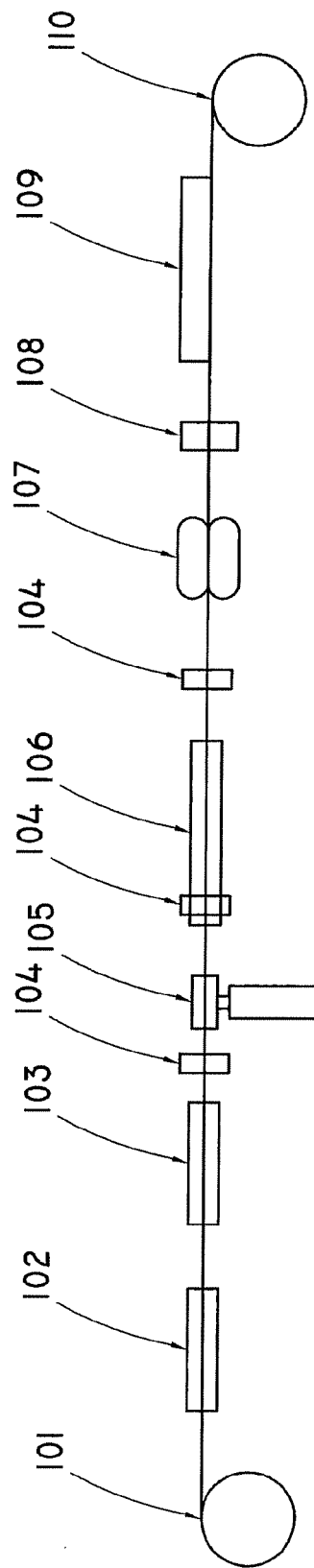
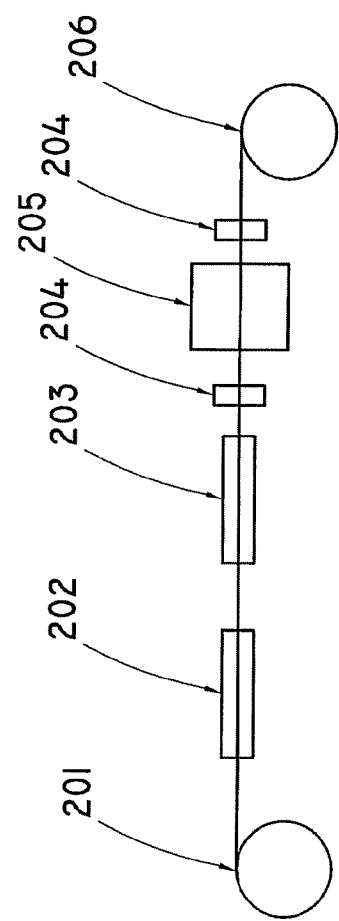

METHOD OF FORMING REINFORCED TUBING

BACKGROUND

1. Technical Field

This invention relates to the field of reinforced tubing for medical applications. More particularly, the invention relates to a method of forming reinforced tubing, and to tubing formed by the inventive method.

2. Background Information

Numerous advances of considerable note have occurred in medical surgical techniques over the last few decades. Among the most significant advances has been the adoption, and now-routine performance, of a variety of minimally invasive procedures. Such procedures include angioplasty, endoscopy, laparoscopy, and arthroscopy, as well as numerous other diagnostic and therapeutic operations. These minimally invasive procedures can be distinguished from conventional open surgical procedures in that access to a site of concern within a patient is achieved through a relatively small incision, into which a tubular device (e.g., an introducer sheath) is inserted or introduced. The tubular device, or device portion, keeps the incision open while permitting access to the target site via the interior (i.e., the lumen) of the device.

Body passageways in which introducer apparatuses have been used to introduce medical interventional devices and/or liquid medicaments include the esophagus, trachea, colon, biliary tract, urinary tract, and virtually all portions of the vascular system, among others. One common example of a minimally invasive technique involves the temporary or permanent implantation of a medical interventional device, such as a stent, into a body passageway of a patient. Other examples involve the transmission of a liquid medicament to a target area, and/or the withdrawal of body fluid from the body passageway.

When carrying out these, and other, desired techniques, communication with the passageway is typically attained by inserting a tubular access device, such as an introducer sheath, into the body passageway. One typical procedure for inserting the introducer sheath is the well-known Seldinger percutaneous entry technique. In the Seldinger technique, a needle is initially injected into the passageway, such as a vessel, and a wire guide is inserted into the vessel through a bore of the needle. The needle is withdrawn, and an introducer assembly is inserted over the wire guide into the opening in the vessel.

Typically, the introducer assembly includes an outer introducer sheath, and an inner dilator having a tapered distal end that extends beyond (i.e., distal to) the distal end of the introducer sheath. The tapered end of the dilator stretches the opening in the vessel in controlled fashion, so that introduction of the larger diameter introducer sheath may then be carried out with a minimum of trauma to the patient. Following satisfactory placement of the introducer sheath, the dilator is removed, leaving at least the distal portion of the larger diameter introducer sheath in place in the vessel. The medical interventional device, e.g., a stent, or a liquid medicament may then be passed through the introducer sheath for delivery to the target site.

Historically, percutaneous insertion techniques were problematic, due in large part to the lack of flexibility and/or kink resistance of the sheath. Early sheaths were generally formed of a relatively stiff fluoropolymer, such as polytetrafluoroethylene (PTFE) or fluorinated ethylene propylene (FEP). The sheaths were typically of thin-walled construction, and were prone to kinking, particularly when threaded through tortuous pathways within the body. Increasing the thickness of the sheath only minimally improved the kink resistance of the sheath. At the same time, the added thickness occupied valuable space in the vessel, thereby minimizing the diameter of the interventional device that could be passed therethrough. In addition, increasing the thickness of the sheath necessitated the use of a larger entry opening than would otherwise be required.

A kinked sheath is essentially unusable, and generally cannot be straightened while positioned in the body of the patient. Consequently, once a sheath kinks, the sheath must be removed, leaving an enlarged, bleeding opening which typically cannot be reused. Access to the vessel must then be re-initiated at an alternative site, and the process repeated with a new sheath. In some cases, a suitable alternative site is not available, and the percutaneous procedure must be abandoned altogether in favor of a different, and often more intrusive, technique.

In recent years, introducer sheaths have been improved in order to enhance their flexibility and kink resistance. Such sheaths are now routinely used to percutaneously access sites in the patient's anatomy that previously could not be accessed with existing sheaths, or that could be accessed only upon the exercise of an undesirable amount of trial and error, with the concomitant discard of sheaths whose placement had been unsuccessful. One example of a flexible, kink resistant introducer sheath is described in U.S. Pat. No. 5,380,304. The sheath described in this patent includes a lubricious inner liner having a helical coil fitted over the liner. A polymeric outer jacket, e.g., a polyether block amide, a polyamide (e.g., nylon), or urethane, is fitted over the coil and liner. The entire assembly is then typically placed in a heat shrink enclosure, and subjected to sufficient heat to melt the outer jacket. The melted outer jacket bonds to a roughened outer surface of the liner through the coil turns. The coil reinforcement imparts kink resistance to this thin-walled sheath through a wide range of bending.

U.S. Patent Publication No. 2001/0034514 discloses an introducer sheath similar in many respects to the sheath of the '304 patent. The sheath in the patent publication is formed such that the proximal end of the sheath has a higher stiffness, while the distal end has a lower stiffness. Since the distal portion of the sheath has a lower stiffness (and therefore is more flexible) than the proximal portion, the sheath is able to traverse portions of the anatomy that would have been difficult, if not impossible, to traverse with stiffer sheaths. Since the proximal portion has a higher stiffness (and is therefore less flexible) than the distal portion, the sheath maintains sufficient trackability to traverse tortuous areas of the anatomy. This presence of the coil reinforcement also enables this sheath to be kink resistant through a wide range of bending angles.

The development of introducer sheaths, such as those described above, has revolutionized the practice of medicine. In particular, these advances have enhanced the ability of the physician to introduce medical interventional devices and liquid medicaments into target sites that had previously been difficult, if not impossible, to reach without the necessity of carrying out much more intrusive open surgical operations. The percutaneous methods described are generally less expensive than the open surgical methods previously employed, are less traumatic to the patient, and typically require a shorter patient recovery time.

In many introducer sheaths, such as the sheaths described in the incorporated-by-reference patents, the lubricious inner liner may be formed of PTFE. PTFE is advantageous because it provides a slippery, low friction inner surface to ease insertion and/or withdrawal through the sheath passageway of a dilator or a medical interventional device, such as a stent. PTFE also has high chemical resistance and inertness, and low thrombogenicity. However, due to this chemical resistance and inertness, PTFE does not bond particularly well with other polymers, such as the polymeric materials used for the outer jacket of the sheath.

Sheaths such as those described above have been well-received in the medical community. These sheaths have greatly enhanced the ability of the physician to utilize less traumatic percutaneous procedures in situations wherein open surgical procedures may have been previously required. Notwithstanding the benefits that have been achieved by the use of such introducer sheaths, new challenges continue to be faced. For example, preparation of such sheaths is a highly labor intensive operation. The sheaths must be individually prepared, generally by hand, wherein one sheath at a time is assembled, and melted as described. This results in an expensive product, which increases the cost of the medical procedure. This cost is increased even further if more than one sheath is necessary in order to accomplish a particular procedure. In addition, due to the general chemical inertness and lack of reactivity of the PTFE liner, the strength of the bond between the PTFE and the outer polymeric layer may be less than optimal. This may result in a higher percentage of rejects during the manufacturing process than desired. This, of course, also increases the cost of the medical procedure.

It is desired to provide a method of forming a reinforced tubular member that overcomes the problems of the prior art. It is also desired to provide a tubular member formed by the inventive method.

BRIEF DESCRIPTION OF THE DRAWINGS

FIG. 1 is a side view of a reinforced tubular member formed according to an embodiment of the inventive method, shown in combination with a conventional hub and side arm;

FIG. 2 is an enlarged, partially sectioned view of the reinforced tubular member of FIG. 1;

FIG. 3 is a process schematic of a coating operation used in one embodiment of the inventive method; and FIG. 4 is a process schematic of a coiling operation used in one embodiment of the inventive method.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

In the following discussion, the terms "proximal" and "distal" will be used to describe the opposing axial ends of a reinforced tubular member, as well as the axial ends of various component features. The term "proximal" is used in its conventional sense to refer to the end of the tubular member (or component thereof) that is closest to the operator during use of the tubular member. The term "distal" is used in its conventional sense to refer to the end of the tubular member (or component thereof) that is initially inserted into the patient, or that is closest to the patient during use.

FIG. 1 shows an illustrative reinforced tubular member 10 of a type that may be formed according to the inventive method. Among other uses, tubular member 10 may be utilized as an introducer sheath of the type commonly used in the medical arts for accessing body passageways of a patient for implantation of a medical interventional device, such as a stent, into the passageway. When used as an introducer sheath, tubular member 10 is typically introduced over a wire guide (not shown) that has previously been inserted into the body passageway in conventional fashion, such as via the Seldinger percutaneous entry technique. Tubular member 10 includes an outer jacket 12, having a distal portion 13 and a proximal portion 15. Preferably, distal portion 13 tapers to a tapered distal end 14. An inner lumen or passageway 16 (FIG. 2) extends through tubular member 10 in well-known fashion.

As indicated in FIG. 1, tubular member 10 may be equipped with a hub 20. Hub 20 may include one or more valves (not shown) positioned therein in well-known fashion. Typically, the valves comprise conventional check-flow type disk valves, and/or a hemostatic valve for preventing the backflow of fluids therethrough. Hub 20 may include a side arm 22 extending therefrom, to which a connecting tube 24 and a conventional connector 18 may be engaged in well-known fashion for introducing and/or aspirating fluids therethrough.

FIG. 2 is a partially sectioned, enlarged, view of the tubular member 10 of FIG. 1. The hub and side arm have been omitted from FIG. 2. Preferably, proximal tube end 15 has a gentle flare as shown. As illustrated, tubular member 10 also comprises an inner liner 21, a reinforcing member such as flat wire coil 23 fitted around the inner liner, and an outer jacket 12 connected to the outer surface 26 of the inner liner.

The inner liner of most conventional layered introducer sheaths is typically formed of a lubricious fluoropolymer, such as PTFE. PTFE has a slippery, low friction inner surface to ease insertion and/or withdrawal through the sheath passageway of a dilator or a medical interventional device, such as a stent. The low friction surface also has high chemical resistance and inertness, and low thrombogenicity.

Conventional introducer sheaths of the type having a PTFE inner liner, a coil reinforcement, and an outer polymeric jacket, are typically individually formed by a highly labor-intensive batch process. Since PTFE is a thermoset material, it is not amenable to formation as part of a continuous process, such as extrusion. Rather, each PTFE length is typically formed by molding the tube from PTFE resin, and individually cutting a segment to an appropriate length for use in the batch process. In the prior art process, the tubular inner liner is generally slid over a cylindrical mandrel having an outer diameter only slightly smaller than the inner diameter of the liner. Next, the reinforcing member, such as a coil, is wound, compression fitted, or otherwise applied over the outer surface of the inner liner. The outer polymeric layer is thereafter slid over the coil and the inner liner.

The entire structure is then typically enveloped in a heat shrinkable enclosure formed of a material such as FEP, and the resulting assembly is placed in an oven. The assembly is then exposed to sufficient heat in the oven to melt the outer layer (but not the inner PTFE liner). As the outer layer melts, it is squeezed by the shrinking FEP enclosure such that it bonds to the roughened outer surface of the inner liner through the respective coil turns. Following the heat shrink application, the heat shrink tube is skived away from the sheath and the mandrel is removed. Further details of prior art processes are described in the incorporated-by-reference patent publications.

Sheaths formed by the prior art process are individually made (i.e., by a batch process), and as indicated by the description provided above, the process is highly labor intensive. As a result, the sheath has a relatively high cost. In addition, the respective inner and outer layers of the sheath rely on the integrity of the bond formed therebetween as a consequence of the heat shrink. Many of the factors that make PTFE a desirable liner material, such as its chemical resistance and inertness, contribute to the difficulty of forming a more secure bond between the inner liner and the outer jacket. If a satisfactory bond is not achieved, the sheath is discarded.

In the inventive method described herein, the tubular members can be formed by a continuous process, as contrasted from the individualized prior art batch process typically used to form the sheaths described above. The inventive method for forming the sheaths is considerably less labor intensive than the prior art methods described herein, resulting in a sheath that can be formed at lower cost when compared to conventional sheaths. In addition, the inventive method utilizes inner and outer layer components that are amenable to the formation of a very reliable bond therebetween.

The inner liner of the tubular member formed according to the inventive method comprises a functionalized polymer. As used herein, the term "functionalized polymer" generally refers to an extrudable polymeric material that has been modified by the incorporation of one or more functional groups. The functional groups provide the polymer with an affinity to form a secure bond with another polymer under reaction conditions at which a non-functionalized polymer would not normally be capable of forming as secure of a bond with the other polymer.

In most cases, it is envisioned that the functionalized polymer will be a functionalized thermoplastic material. Functionalized thermoplastic fluoropolymers represent a particularly preferred class of functionalized thermoplastic materials for use in the inventive method. Thermoplastic fluoropolymers and copolymers, such as fluorinated ethylene propylene (FEP) and ethylene fluorinated ethylene propylene (EFEP), are particularly favored due to their high chemical inertness, and low coefficient of friction.

Use of a functionalized polymer, such as a thermoplastic fluoropolymer and copolymer, as an inner liner material provides many benefits when compared to a tubular member formed according to the prior art batch process described above. For example, use of the functionalized polymer enables the tubular members to be formed as part of a continuous process. As a result, an elongated tubular member can be formed and wound around a spool for use in the continuous process. Once the process is carried out as described, the elongated tubular member may be cut to any desired length.

In addition to the ability to utilize the functionalized thermoplastic material in a continuous process, use of the functionalized thermoplastic material typically eliminates the necessity to treat the outer surface of the inner liner by, e.g., chemical etching, mechanical roughening, addition of adhesive, or like methods, to enhance the ability of the inner liner material to form a bond with the outer polymeric jacket. Similarly, use of the functionalized thermoplastic material eliminates the necessity of including a heat shrink step as in the prior art process, thereby avoiding the labor involved in such a step, as well as the necessity of heating in an oven at an elevated temperature.

When utilizing the functionalized thermoplastic polymers, the active functional groups enhance the bonding affinity between the functionalized polymer that comprises the inner liner, and the polymer comprising the outer jacket. As a result, a secure chemical bond can be formed therebetween at a relatively low overall temperature, when compared to the elevated temperature required for the heat shrink in the prior art process. In addition to the formation of a secure bond between the functionalized thermoplastic polymer and the outer jacket, the polymeric inner liner generally retains the lubricity, inertness and chemical resistance typical of such polymers in general.

As stated, in the prior art the inner liner material of choice for tubular members has typically been PTFE. PTFE, a thermoset fluoropolymer, has many favorable characteristics for use in a tubular sheath, such as chemical inertness and a very low coefficient of friction. However, PTFE is not conducive to production in tubular form in a continuous process. Thus, sheaths having a PTFE liner are virtually always formed in a labor intensive batch process.

Non-limiting examples of functionalized polymers and copolymers suitable for use herein are described in, among other sources, U.S. Pat. Nos. 6,911,509 and 7,220,807, both incorporated by reference herein. The '807 patent describes several processes for preparing suitable fluoropolymers and copolymers. In one such process, functionalized polymers are formed by combining one or more functional fluoromonomers with a polymerization initiator, such as an organoborane (e.g., a trialkylboroane), and oxygen to polymerize the fluoromonomer into a functional fluoropolymer.

According to the patent, any fluorinated functional monomer is believed to be suitable for polymerization as described. An example provided comprises functional fluoromonomers having the following formula:

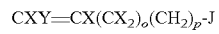

$$CXY=CX(CX_2)_o(CH_2)_p-J$$

wherein X and Y are independently hydrogen, fluorine and chlorine; o is 0 to 10; p is from 1 to about 6; and J is a functional group, provided that at least one X or Y is a fluorine and preferably where X and Y represent fluorine. In one embodiment, J is selected from the group consisting of: OH, halogen (i.e., Cl, Br), ester, epoxy, thiol, $SO_3H$, $SiR_1R_2R_3$, and an olefinic group, where $R_1$, $R_2$, and $R_3$ are independently H, halogen (i.e., Cl), a $C_1$ to $C_{10}$ linear, branched, cyclic alkyl or aryl group. Other functional fluoromonomers said to be useful include trifluorovinyl functional monomers. Many suitable monomers are commercially available or readily derivable from commercial starting compounds.

A variation of this process for preparing a functional fluoropolymer comprised combining a fluoromonomer with oxygen and an organoborane functional initiator, wherein the organoborane contained a functional group.

In another process discussed in the '807 patent, multiple functional fluoromonomers can be copolymerized alone or in combination with one or more non-function fluoromonomers to form an array of fluoro-copolymers having pendent functionality. Functional fluoropolymers such as those polymerized using the organoborane initiator have functional pendent groups containing allylic proton(s), an Si—H group, or an cinnamoyl group. A functional fluoropolymer polymerized using the organoborane functional initiator has a terminal functional group such as $Si(OR)_3$, and OH group, at the beginning of the polymer chain.

Other processes for preparing suitable extrudable compounds for use herein are discussed in the incorporated by reference patents. Typically, suitable functional fluoropolymers and copolymers can be polymerized in high yields for use herein, and to relatively high molecular weights, such as greater than about 5,000 g/mole, and preferably, greater than about 50,000 g/mole.

In addition to preparing suitable extrudable polymers, functionalized polymers suitable for use in the present invention are also commercially available. Functionalized polymers particularly preferred for use in the present invention include the functionalized fluoropolymer FEP, as well as its derivatives, such as EFEP. Functionalized EFEP (ethylene fluorinated ethylene propylene) is available from Daikin America, Inc., of Orangeburg, N.Y. These fluoropolymers are sold under the trademark NEOFLON™. Particularly preferred blends of EFEP include EFEP RP-4020 and RP-5000. EFEP is a copolymer having a low coefficient of friction, high chemical resistance, and is inert to attack by harsh chemicals. It has a high transparency. Additionally, it adheres well to many polymers without the necessity of etching or the use of adhesives.

In addition to the functionalized thermoplastic fluoropolymers described above, other extrudable thermoplastic polymers that have been modified by the addition of a functional group may also be useful in a particular case. One non-limiting example of a polymer that may be functionalized to provide the polymer with an affinity to form a secure bond with another polymer is high density polyethylene (HDPE). HDPE is one example of a number of "tie layer" materials (LLDPE, EVA, are others) that may be utilized to form a functionalized polymer suitable for use herein. Such materials are referred to as "tie layer" materials because they are chemically modified (e.g., typically anhydride modified) in well-known fashion to render them capable of bonding, or "tieing", dissimilar layers of polymers together.

Although tie layer materials are often utilized in commercial applications due to their ability to bond, or tie, other polymers together, in many cases, such as the presently-described application, these materials may be utilized as a suitable sheath material in their own right. Other known extrudable anhydride-modified polyolefins that are capable of bonding with dissimilar polymers as taught herein may also be utilized. Suitable tie layer resins, such as those described herein, are commercially available, e.g., from Lyondell Chemical Company, of Houston, Tex. One such tie layer resin is PLEXAR® PX2049, an extrudable tie layer resin anhydride modified HDPE.

Those skilled in the art will appreciate that other extrudable materials can also be functionalized for use herein by other means known in the art, to enhance their ability to bond with the outer sheath layer. Any such functionalized materials may be substituted for those non-limiting examples specifically referenced herein. In addition, suitable functionalized polymers may be formed by methods other than those specifically recited in the incorporated-by-reference patents, and are available from still other commercial sources. In order to maximize the benefits of the present invention, the functionalized polymer will be extrudable, and have an affinity to form a secure bond with another polymer under conditions at which a non-functionalized polymer would not normally be capable of forming as secure a bond with the other polymer.

Preferably, the reinforcing member is a helical coil. The coil 23 may be formed from compositions typically used in the medical arts for such purpose, such as a metal, a metal alloy (e.g., stainless steel or a shape memory composition such as nitinol), a multi-filar material, or a composite material. In order to minimize the cross-sectional profile (i.e., outer diameter) of the tubular member, it is preferred to utilize a coil with a conventional flat wire construction. However, those skilled in the art will appreciate that coil materials of other cross-sectional configurations, such as round, oval, and various other geometric configurations, may be substituted. Other reinforcing structures, such as a braid of a coil/braid hybrid, may be substituted for a coil, or utilized in combination with a coil if desired.

Outer jacket 12 may generally be formed from any composition suitable for use in a tubular medical device, and that is capable of reacting with the functionalized polymer to form a secure bond therewith. Suitable polymers include those polymers commonly used to form an outer layer of an introducer sheath. Non-limiting examples of suitable polymers include polyether block amides, polyamides (nylon), polyurethane, and polyolefins.

Use of a functionalized thermoplastic material, such as the functionalized polymers described above, is amenable to use in a continuous process for formation of reinforced tubing. FIGS. 3 and 4 illustrate schematic diagrams of one example of a suitable process for fabrication of reinforced tubing according to the inventive method. Those skilled in the art will appreciate that other conventional coating (extrusion) and coiling processes may be substituted in a particular case. The systems described in FIGS. 3 and 4 are not intended to be exclusive, but rather, illustrative of possible processes for forming reinforced tubing within the scope of the present invention. Additional steps may be added to the systems as described and illustrated in FIGS. 3 and 4 if desired. Alternatively, not every step described and illustrated herein need be carried out in every instance. It is believed that those skilled in the art can readily fashion an appropriate fabrication scheme for a particular process, when taking into account the features of the present invention.

FIG. 3 illustrates a schematic diagram of one coating process suitable for use in forming the reinforced tubular member. In the present example, the coating system depicted in FIG. 3 may be utilized for coating (extruding) the inner liner onto a mandrel, and then again for coating the outer jacket onto the inner liner following winding of the coil over the liner. FIG. 4 illustrates a process schematic of a suitable coiling process.

The process schematic of FIG. 3 includes process steps 101-110. As stated above, not every one of steps 101-110 need be carried out in every instance, as the process illustrated and described in FIG. 3 is only intended to represent one possible operational sequence. Those skilled in the art will appreciate that minor modification may be made to some steps, other steps may be omitted altogether in some instances, and still others (e.g., the measurement step) may be repeated at various times during the sequence.

In the system illustrated in FIG. 3, unspooling device 101 comprises a mandrel that is wound onto a conventional spool. The term "mandrel" is used herein to describe a wire or core that is initially wound around the spool, and that is thereafter unwound to form an inner core in the coating (extrusion) process to be described.

Those skilled in the art can readily select a suitable mandrel for use as an inner core for an extrusion process. One preferred example in the inventive method is an acetal mandrel. Acetal mandrels are known in the art, and are commercially available, e.g., from Precision Extrusion, Inc., of Glen Falls, N.Y. Other suitable mandrel compositions include various metals and metal alloys, such as copper or stainless steel, and other polymeric materials (e.g., PEEK, nylon, etc.) Preferably, the mandrel will have an outer diameter of, for example, between about 1.5 and 3 mm.

As the mandrel unwinds from the spool, it may be passed through a heating device 102. Heating device 102 is provided to eliminate the "set" in the mandrel. Typically, upon being wound onto the spool of unspooling device 101, the mandrel takes on a permanent, or semi-permanent, curve, or set, which is preferably eliminated prior to further processing. When the mandrel is a polymer, one way of removing the set is to pass the mandrel through a heating device. The heating device heats the polymer to a temperature sufficient to remove the set and straighten the polymer, but less than a melting temperature for the polymer. Heating devices for use in extrusions are well known in the art, and those skilled in the art can readily select an appropriate heating device, as well as determine an appropriate amount of heat for a particular polymer.

If the mandrel is a metal, or metal alloy, the set is typically removed utilizing a wire straightener, rather than a heating device. In this instance, a heating device is generally neither necessary nor helpful. Instead, a wire straightener may be used to remove any set or curve in the mandrel. Wire straighteners are well known in the art, and any conventional straightener may be utilized to remove the set from the wound metal or metal alloy mandrel wire.

An applicator 103 may be provided for applying an optional lubricant to the mandrel. Once the reinforced tubular member is formed according to the inventive method, it will, of course, be necessary to remove the mandrel from the inner lumen of the reinforced tubular member. Application of a small amount of a lubricant, such as silicone, to the outer surface of the mandrel facilitates its later removal. One preferred type of applicator is a conventional circular brush that is capable of applying lubricant in a circumferential manner around the surface of the mandrel.

Depending upon the particular mandrel and functionalized polymer selected for use as an inner liner material, a lubricant may also be useful for inhibiting any reaction between the mandrel and the functionalized polymer of the inner tubular layer. For example, when a polymeric mandrel is utilized, such as the acetal mandrel described above, the reactivity of a functionalized thermoplastic polymer may enable a certain amount of bonding to occur between the functionalized polymer and the mandrel. Such bonding is undesirable, as it complicates the later removal of the mandrel from the tubular member. The presence of the lubricant inhibits bond formation between the fluoropolymer and the mandrel.

A measurement device 104 may be provided for measuring the diameter of the mandrel prior to extrusion of the functionalized polymer over the mandrel wire. Those skilled in the art will appreciate that it is desirable to measure the diameter of the mandrel prior to extrusion of the functionalized polymer, so that the thickness of the polymeric layer may be monitored. Typically, measurement device 104 comprises a multi-axis laser scanner of a type well-known in the art.

A coating device, such as extruder 105, is provided for coating the functionalized polymer onto the lubricated mandrel. Extrusion devices capable of melting functionalized polymers, such as the functionalized thermoplastic polymer resins described herein, and coating a mandrel wire with the melted plastic, are well known in the medical arts, and a skilled artisan can readily select an appropriate device for a particular use. A typical extruder may have a 1.25 inch (3.2 cm) diameter×24/1 length to diameter ratio, with a screw speed range of 1-100 rpm. Suitable extrusion devices are available commercially from, e.g., American Kuhne, Inc., of Ashaway, R.I., USA.

A cooling device 106 is provided for cooling the extruded plastic. Typically, cooling device 106 comprises a (deionized) water trough through which the extrusion is passed. Other conventional cooling devices for use in extrusion, such as an enclosure of chilled air, may be substituted. A second measurement device 104 may also be positioned in the cooling device for measuring the diameter of the extruded coating on the mandrel.

If desired, a further measurement device 104 may be provided downstream of the cooling device for measuring the diameter of the cured plastic coating on the mandrel. With the exception of the measurement device in the cooling device as described above, this and all other measurement devices described herein may be multi-axis laser scanning devices. These devices are capable of providing a digital read-out of the diameter within an acceptable level of accuracy. One example of a measuring device that may be used in the cooling trough is a Beta Lasermic DataPro 5000 with ultrasonic measuring capabilities.

A haul off/pulling device 107 is provided for pulling the extrudate down the line. This device controls the diameter of the product. Size is determined by the difference in the rate of the extruder output vs. the pulling rate. One example of a suitable such device is the RDN Puller/Cutter System Model #IC2-218-3, available from RDN Manufacturing Co., Inc., of Bloomingdale, Ill.

Cutting mechanism 108 and conveyor/part collection device 109 illustrated in FIG. 3 are bypassed at this time, and the coated mandrel is directly passed from the haul off/pulling device 107 to, and wound around, spooling device 110. Spooling device 110 comprises the coated mandrel wound onto a spool.

The spooling device 110 comprising the coated mandrel may be manually transferred to the coiling system of FIG. 4 for further processing. At this stage, spooling device 110 is referred to as unspooling device 201, since the coated mandrel (of spooling device 110) is now unwound from the spool as it passes through the coiling system. Although the following discussion involves the manual transfer of spooling device 110 (i.e., unspooling device 201) to a discrete coiling unit as depicted in FIG. 4, those skilled in the art will appreciate that a separate unit need not be utilized. Rather, if desired, the coiling system of FIG. 4 may represent a continuation of the coating system depicted in FIG. 3.

A heating device 202 is provided for receiving the coated mandrel. Heating device 202 is utilized for similar purposes as heating device 102 in FIG. 3, namely, for heating the coated mandrel to remove any set, or curvature, in the line resulting from winding onto spooling device 110 (unspooling device 201). In addition to the foregoing, heating device 202 has another function. As the coated mandrel is passed through the heating device, the extruded functionalized polymer coating is softened. Softening the polymer coating prior to winding the coil thereon permits the coil to sink a small distance into the softened outer diameter of the extruded functionalized polymer. This serves to "lock" the coil into a specific position along the outer surface of the polymer. In addition, sinking the coil a small distance into the inner polymeric liner as described may result in a sheath having a lower profile when compared to sheaths formed by conventional processes.

An optional applicator 203 may be provided for applying a small amount of an adhesive to the outer surface of the extruded polymer. Adhesive applicators are well known in the art, and any conventional applicator, such as a circular brush, will typically be suitable. When utilized, the adhesive inhibits substantial movement, or drifting, of the coil following its application onto the polymer. Typically, only a minimal amount of adhesive is applied, so as to not appreciably affect the outer profile of the device. Those skilled in the art will appreciate that in this context an adhesive could represent a thermoplastic polymer that has a natural affinity to adhere, such as a low durometer polyether block amide (e.g., PEBAX®) or polyamide (e.g., GRILAMID® or VESTAMID®), or a coextrudable adhesive polymer (e.g., BYNEL®).

A measurement device 204 may be provided for measuring the diameter of the fluoropolymer coating having the adhesive applied thereto. As stated above, measurement device 204 may be a multi-axis laser scanning device.

A coiling mechanism 205 is provided for applying a coil to the outer surface of the extruded polymeric coating. Coiling mechanisms are known in the art, and those skilled in the art can readily select an appropriate mechanism for use herein. In this procedure, the coiling mechanism is a continuous coiler that is capable of feeding a tubular structure through the center of the mechanism in order to coil over the tubular structure. Preferably, the coiler is also capable of spooling up the coiled over material. Suitable continuous coilers are available, e.g., from Steeger USA, of Inman, S.C., as Model # HS-KL/1035-60IMC.

Preferably, coiling mechanism 205 will be capable of winding a coil along the outer surface of the extruded functionalized polymer that includes uniformly spaced coil turns, and wherein the coil turns also have a constant pitch. As stated above, the coiling wire used in the coiling mechanism 205 is preferably stainless steel flat wire, although were of other compositions and configurations may be substituted. The coiled polymer may then be passed through another measurement device 204, and thereafter wound onto a spooling device 206.

Spooling device 206 is now ready for application of the outer polymeric jacket. In the system of FIGS. 3 and 4, spooling device 206 is returned to the coating system of FIG. 3, at which time it becomes spooling device 101. In this instance, spooling device 101 comprises the mandrel having the functionalized polymer extruded thereon, and further having the coil wound thereon.

The coating process for coating the outer polymeric jacket is generally similar to that for coating the functionalized polymer as described previously. In this case, however, the coating device (extruder) 105 is equipped with a particular polymeric resin suitable for forming the outer layer of the reinforced tubular member.

Importantly, the polymeric resin for forming the outer jacket must be reactive with the extruded functionalized polymer, such that a secure bond is formed therebetween upon extrusion of the outer jacket polymer over the functionalized polymer. When the functionalized polymer is a fluoropolymer formed of a composition such as EFEP RP-4020 and RP-5000, as described above, the outer jacket is typically formed from a polyamide (nylon) or a polyether block amide, a polyurethane or a polyolefin. These compositions are well known for use in medical tubing, such as introducer sheaths, and are capable of forming a secure bond with these functionalized fluoropolymers. Those skilled in the art will appreciate that other polymers suitable for use as an outer jacket material may be substituted in a particular case.

This coating process for the outer polymer jacket differs from the coating process for the functionalized polymeric inner liner, in that two additional steps are typically carried out. These are illustrated by 108 and 109 in FIG. 3. Once the polymeric outer jacket material is extruded onto the coiled functionalized polymer, fabrication of the reinforced tubular member is substantially complete. At this time, following passage through the haul off/pulling device 107, the elongated tubular thread comprising the functionalized polymer, coil, and outer polymeric jacket is cut to size. The tubular member is passed through a cutting mechanism (knife) 108 which has been pre-set to cut the elongated tubular member into individual tubes of a desired length. An optional collection device 109 may be provided for receiving the cut tubes.

Final processing involves pulling out the mandrel, and any final trimming of the outer edges of the tubular member to size. Typically, the mandrel is removed by hand.

Although the coating system depicted in FIG. 3 may be utilized herein to apply both the functionalized polymeric inner liner and the polymeric outer jacket as described, these operations need not be combined in a single system. Rather, if desired, following the coiling step as depicted in FIG. 4, the coiled polymer may be transmitted to another system for application of the polymeric outer jacket. Although there may be an economy of space and cost by utilizing the same extrusion equipment for each coating step as described above, there may also be some benefit to using separate systems. For example, when separate systems are used, the system for coating the mandrel with the polymer remains available for use at all times, and is not otherwise engaged with extruding the outer jacket. Similarly, cleaning of the extrusion equipment system may be facilitated if the equipment is only used for extrusion of one particular polymer, or other closely related polymers. Generally, however, it is believed that the economies achieved in using the same system for both extrusions will outweigh those of separate systems in most instances.

Those skilled in the art will appreciate that additional steps may be added to the process in order to incorporate additional features into the finished product. For example, it may be desired to form an outer layer 12 comprising a plurality of tube segments having different stiffnesses. In this case, the segments will typically be aligned in order of decreasing stiffness in the direction of the distal end of the sheath.

Thus, for example, it may be desired to have a stiffer proximal section of the outer jacket comprised of a relatively high durometer material, a more flexible distal section comprised of a relatively low durometer material, and optionally, one or more intermediate sections positioned between the proximal and distal sections having decreasing stiffnesses between the proximal and distal sections. This may be accomplished, e.g., by adding one or more additional extruders 105 to the coating head. In this case, the respective extruders would have different durometer materials in them, and the system would be programmed to switch from one extruder to another, depending on the particular durometer that is desired for a discrete length of the product. Therefore, a product can be formed to have as many different durometers (stiffnesses) as may be desired along the length of the product.

Those skilled in the art will appreciate that additional coatings, treatments, etc., as may be common with medical devices, may be applied to the reinforced tubular member. For example, it may be desired to apply a hydrophilic coating to a portion of the exterior surface of the tubular member. This may be accomplished by adding such coating as a separate step along the system of FIG. 3, to be applied following extrusion of the outer jacket. Alternatively, a hydrophilic coating may be applied as a final processing step before or after the tubes are cut to size. Similarly, for example, a radiopaque marker band may be applied to the outer surface of either the inner liner or the outer jacket. Radiopaque markers and hydrophilic coatings are widely used in connection with introducer sheaths, and further description of these features is not necessary to provide an understanding of the present invention. Further description of such sheaths, and their methods of manufacture, are provided in the incorporated-by-reference patent documents.

The details of the construction or composition of the various elements of the introducer sheath 10 of the present invention not otherwise disclosed are not believed to be critical to the present invention, so long as the recited elements possess the strength or mechanical properties needed for them to perform as disclosed. Many such details not described herein are recited in detail in the incorporated-by-reference patent documents. Additional details of construction are believed to be well within the ability of one of ordinary skill in the art.

It is therefore intended that the foregoing detailed description be regarded as illustrative rather than limiting, and that it be understood that it is the following claims, including all equivalents, that are intended to define the spirit and scope of this invention.

The invention claimed is:

1. A method of forming a reinforced tubular medical device in a continuous operation, comprising:
   providing an elongated core capable of movement along a line, wherein said elongated core comprises a polymeric material;
   unwinding said elongated core from a spool and heating said elongated core to remove a set of said elongated core;
   forming an elongated tubular member around a moving length of said core, said elongated tubular member formed by:
      applying a coating of a functionalized polymer around said moving length of said core, said functionalized polymer comprising functional groups,
      applying a reinforcing member to an outer surface of said functionalized polymer coating along said moving length, and
      applying a polymeric outer jacket over said functionalized polymer and said reinforcing member along said moving length, said functional groups enhancing bonding affinity between said functionalized polymer and said polymeric outer jacket, whereby a bond is formed between said functionalized polymer and said polymeric outer jacket;
   cutting said elongated tubular member to form said tubular medical device; and
   removing the elongated core from said device.

2. The method of claim 1, wherein the functionalized polymer is applied around said moving core length by extrusion.

3. The method of claim 2, wherein the functionalized polymer comprises a thermoplastic polymer.

4. The method of claim 3, wherein the thermoplastic polymer comprises a fluoropolymer.

5. The method of claim 2, wherein the functionalized polymer comprises ethylene fluorinated ethylene propylene.

6. The method of claim 2, wherein the functionalized polymer comprises high density polyethylene.

7. The method of claim 2, wherein the polymeric outer jacket is applied over said functionalized polymer and said reinforcing member by extrusion.

8. The method of claim 7, wherein said polymeric outer jacket comprises a polyether block amide, a polyamide, a polyurethane, or a polyolefin.

9. The method of claim 1, wherein the step of applying the reinforcing member comprises winding a wire around said functionalized polymer to form a coil or a braid reinforcement.

10. The method of claim 1, wherein said elongated core comprises acetal, said functionalized polymer comprises fluorinated ethylene propylene, and said reinforcing member comprises a flat wire coil.

11. The method of claim 2, wherein said functionalized polymer coating and said elongated core are collected on a spool, and wherein said reinforcing member is applied to the outer surface of said functionalized polymer as said functionalized polymer and said elongated core are unwound from said spool.

12. The method of claim 11, wherein said functionalized polymer coating and said reinforcing member are collected on a second spool.

13. The method of claim 12, wherein said polymeric outer jacket is applied by extrusion as said functionalized polymer and reinforcing member are unwound from said second spool.

14. The method of claim 1, further comprising applying a lubricant to said core prior to applying said functionalized polymer coating.

15. The method of claim 14, wherein said lubricant inhibits bonding between said functionalized polymer and said core.

16. The method of claim 15, wherein said functionalized polymer is applied around said moving core length by extrusion.

17. The method of claim 16, wherein said functionalized polymer comprises a thermoplastic fluoropolymer.

18. The method of claim 11, further comprising the step of softening the functionalized polymer coating prior to applying said reinforcing member.

* * * * *